(12) United States Patent  (10) Patent No.: US 8,552,722 B2
Lionheart et al.  (45) Date of Patent: Oct. 8, 2013

(54) DETECTOR SYSTEMS

(75) Inventors: William Robert Breckon Lionheart, High Peak (GB); Anthony Peyton, Greater Manchester (GB); Xiandong Ma, Lancaster (GB)

(73) Assignee: Rapiscan Systems, Inc., Torrance, CA (US)

( * ) Notice: Subject to any disclaimer, the term of this patent is extended or adjusted under 35 U.S.C. 154(b) by 414 days.

(21) Appl. No.: 12/523,051

(22) PCT Filed: Jan. 15, 2008

(86) PCT No.: PCT/GB2008/000116
§ 371 (c)(1),
(2), (4) Date: Apr. 19, 2010

(87) PCT Pub. No.: WO2008/087385
PCT Pub. Date: Jul. 24, 2008

(65) Prior Publication Data
US 2010/0207624 A1  Aug. 19, 2010

(30) Foreign Application Priority Data

Jan. 15, 2007 (GB) .................................. 0700731.3
Feb. 22, 2007 (GB) .................................. 0703481.2

(51) Int. Cl.
*G01R 33/02* (2006.01)

(52) U.S. Cl.
USPC ....................................................... 324/258

(58) Field of Classification Search
USPC ................. 324/228, 243, 244, 258, 345, 347; 340/551, 552, 572.1, 572.2, 572.4, 340/572.5, 572.6, 572.7, 572.8; 361/180
See application file for complete search history.

(56) References Cited

U.S. PATENT DOCUMENTS

| 6,819,241 | B2 * | 11/2004 | Turner et al. ................... 340/551 |
| 2003/0080868 | A1 * | 5/2003 | Nelson ........................... 340/551 |
| 2004/0000999 | A1 * | 1/2004 | Turner et al. ................. 340/572.4 |
| 2004/0012494 | A1 | 1/2004 | Lee |
| 2004/0080315 | A1 | 4/2004 | Beevor et al. |
| 2009/0232353 | A1 * | 9/2009 | Sundaresan et al. .......... 382/103 |

FOREIGN PATENT DOCUMENTS

| CN | 1245295 | 2/2000 |
| DE | 19907758 | 8/1999 |
| WO | WO 97/01771 | 1/1997 |
| WO | WO 03/048808 | 6/2003 |
| WO | WO 2004/097456 | 11/2004 |

OTHER PUBLICATIONS

PCT Search Report PCT/GB2008/000116, Jul. 24, 2008, Rapiscan Systems, Inc.

* cited by examiner

*Primary Examiner* — Melissa Koval
*Assistant Examiner* — Daniel Miller
(74) *Attorney, Agent, or Firm* — Novel IP

(57) ABSTRACT

A detection system comprising a plurality of magnetic field generators and a plurality of magnetic field detectors located adjacent to a detection area, and a control system arranged to generate magnetic field using the generators, and, for each of the generators, to make measurements of the magnetic field generated using each of the detectors, and processing means arranged to process the measurements to generate a data set characterising the detection area.

18 Claims, 6 Drawing Sheets

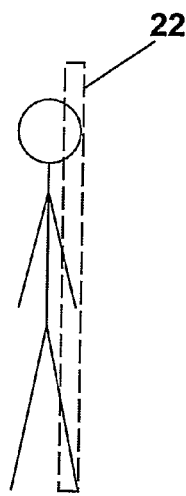 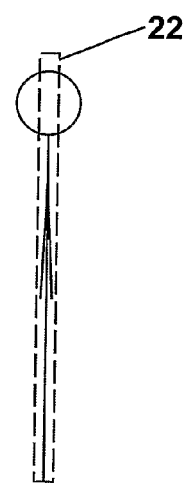 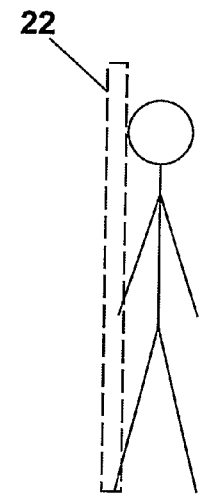
*Fig. 9a*   *Fig. 9b*   *Fig. 9c*
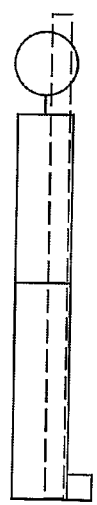 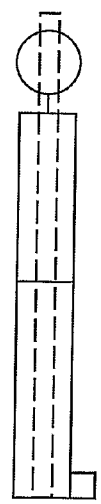 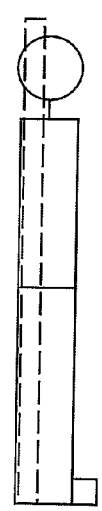
*Fig. 10a*   *Fig. 10b*   *Fig. 10c*

DETECTOR SYSTEMS

CROSS-REFERENCE

The present application is a national stage application of PCT/GB2008/000116, which was filed on Jan. 15, 2008, which further rely on two applications filed in Great Britain for priority: UK0700731.3, filed on Jan. 15, 2007, and UK0703481.2, filed on Feb. 22, 2007.

FIELD OF THE INVENTION

The present invention relates to magnetic detection systems, including electromagnetic (EM) detection systems and has particular application in security detection systems including walk-through detectors.

BACKGROUND OF THE INVENTION

It is known to provide walk-through metal detectors comprising an array of transmitter coils and an array of detector coils. These operate using coupling between pairs of coils, providing a multi-zone system with a coil pair for each zone, each pair operating as an independent metal detector. In present systems, the transmitter coils may typically be situated in one panel whereas the receiver coils are in an opposite panel.

Such known systems can detect the presence of metal objects, but have very little ability to discriminate between different types of object.

SUMMARY OF THE INVENTION

The present invention therefore provides a detection system comprising a plurality of magnetic field generators, and a plurality of magnetic filed detectors, which may be receiver coils, located around a detection area, and a control system which may be arranged to generate magnetic field, for example by generating electrical current in the transmitter coils, and may also be arranged to measure the magnetic field at each of the detectors, for example by detecting induced signals in the receiver coils. The system may further comprise processing means arranged to process measurements of the generated field, for example by measuring the induced signals, to generate a data set characterizing the detection area.

The generators may be electrical conductors, i.e. coils, through which electric current can be passed to generate the magnetic field. The detectors may be electrical conductors, i.e. coils, in which an electric current will be generated by changes in magnetic field thereby enabling the field to be detected. Alternatively other forms of magnetic detectors, such as solid state magnetometers, can be used.

The data may be image data arranged to generate an image of the detection area. The image may be a two-dimensional image of a two-dimensional detection area, or a three-dimensional image of a three-dimensional detection area. Alternatively, or at the same time, the data may be characterizing data characterizing the detection area, in which case the processing means may be arranged to analyze the data, for example to detect the presence of a predetermined type of object.

If the data is image data the detection area may be divided into zones which are represented by pixels or voxels in the image, and data from the pixels or voxels, can be combined to form image data. If the data is just characterizing data, then it may also be arranged to relate to a plurality of zones within the detection area. The system may therefore be arranged to generate an alarm for a particular zone but with improved ability to discriminate between large objects far from the generators or detectors and small objects close to the generators or detectors.

The detection system may be a security detection system in which the coils are mounted on support means arranged to allow a person to walk through the imaging area.

The processing means may be arranged to generate a plurality of sets of data as an object moves through the imaging area, and to combine the sets of data to form a resultant data set. The object may, for example, be a person together with their clothing and any articles they are carrying with them.

The detection system may comprise movement sensing means, or position sensing means arranged to measure the position and/or changes in position of at least a part of an object, for example relative to the either the generators or the detectors or another part of the object, and may be arranged to use the changes of position when combining the sets of data. The movement sensing means may be a video camera or other imaging system, or may comprise other forms of sensor such as light sensors in which breaking of a light beam by the object is used to detect the position of the object.

The processing means may be arranged to combine the sets of data to produce a tomographic data set representing a tomographic model or image of the object.

The detection system may comprise displacement sensing means arranged to detect displacement of a part of the object away from a reference position, and to correct for the displacement when combining the sets of data. This sensing means may also comprising an imaging system, such as a video camera, but may also comprise other forms of sensor.

The reference position may be a position relative to at least a part of the object. The displacement may be a displacement relative to at least a part of the object. Preferred embodiments of the present invention will now be described by way of example only with reference to the accompanying drawings in which:

BRIEF DESCRIPTION OF THE DRAWINGS

FIGS. 9a, 9b and 9c show the system of FIG. 1 in a first mode of operation;

FIGS. 10a, 10b and 10c show the system of FIG. 1 in a second mode of operation.

DETAILED DESCRIPTION OF THE INVENTION

Figure 1:
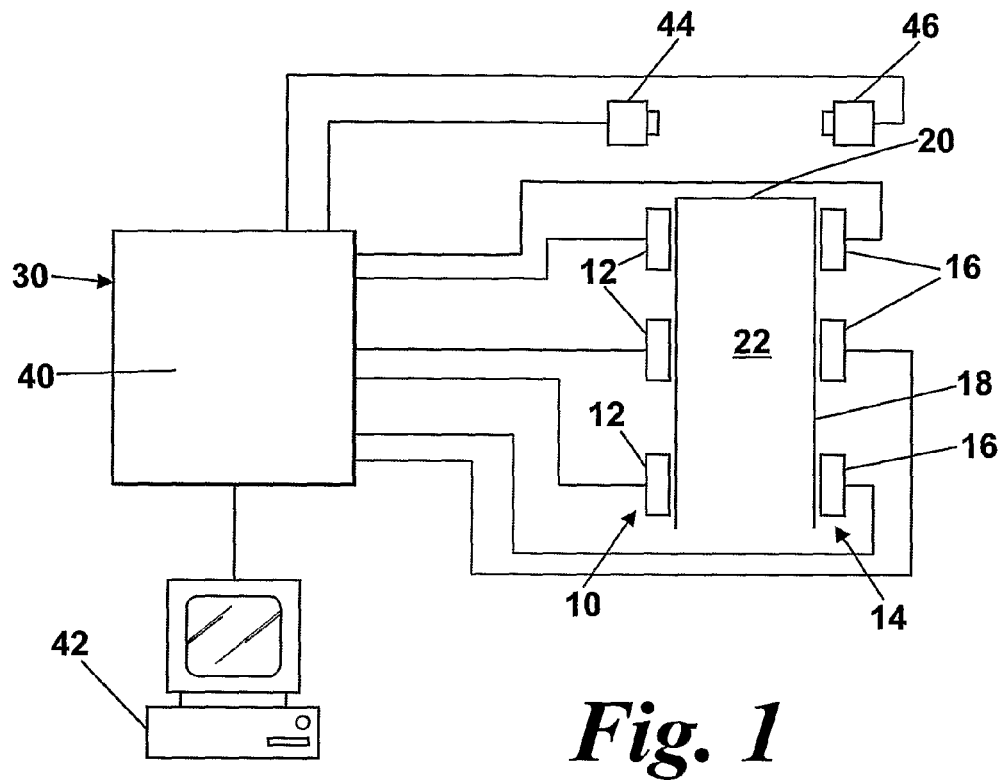
FIG. 1 is a schematic diagram of a detection system according to an embodiment of the invention.
Figure 2:
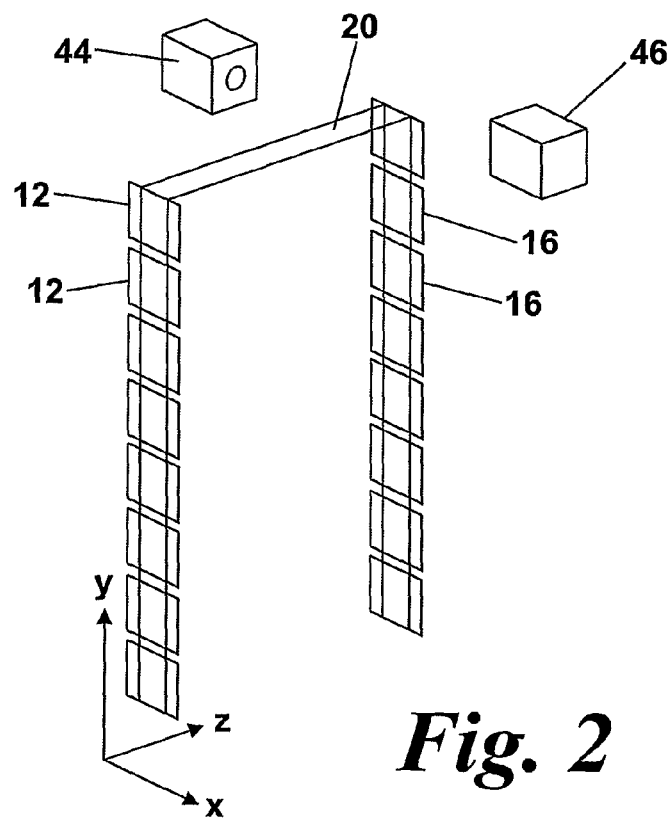
FIG. 2 is a perspective view of the coil arrays of the detection system of FIG. 1.

Referring to FIGS. 1 and 2, a detection system comprises a linear array 10 of transmitter coils 12 and a linear array 14 of receiver coils 16. The arrays 10, 14 are arranged on opposite sides of a support frame 18 which defines an arch or gate 20, within which is an imaging area 22 through which a person can walk. There are equal numbers of transmitter and receiver coils, in this case eight of each, with each transmitter coil 12 being level with and opposite a respective receiver coil 16.

A control system 30 is arranged to generate and control a varying electrical current independently in each of the transmitter coils 12 to generate magnetic fields and, for the field generated from each transmitter coil, to measure signals, in the form of electrical currents, generated in each of the receiver coils 16. The gate size is 220 mm in depth, 2026 mm in height and 860 mm in width, which are assumed to coincide with x-, y-, and z-axis respectively.

Simple square coils are used for both transmitter and receiver coils, each having a size of 220 mm×220 mm square and 1 mm in depth. The coils are equally placed at 38 mm intervals in both panels to preserve symmetry, which makes the tomography analysis easier. The central plane at x=0 mm is assumed as the sensing plane with a size of (0, 0, −380)~(0, 2026, 380).

The control system also includes data acquisition and conditioning electronics 40 arranged to collect data from the receiver coils 16 and a processing system 42, in the form of a host computer, arranged to carry out processing of the conditioned signals from the receiver coils 16 to generate images and perform detection algorithms.

Two video cameras 44, 46 are also provided, one on each side of the gate 20 and orientated so that they both image the imaging area from different angles. The video cameras 44, 46 are also connected to the computer 42. The computer 42 is arranged to process the video image signals it receives from the video cameras 44, 46 and the inductance signals it receives from the receiver coils 16 and process them as will be described in more detail below.

A measurement can be obtained by energizing one of the transmitter coils 12 with a sinusoidally varying AC signal, thereby creating a magnetic field. This magnetic field is modified by electrically conductive or ferromagnetic objects within the field and the resultant field changes are measured with the array of detection coils 16. If the series of transmitter coils 12 is energized sequentially around the object, and for each transmitter coil, the field measured with each of the receiver coils, it is possible to generate an image of the object using adequate reconstruction software by combining the resultant detected signals. The number and positions of detection coils have a significant effect on the image's quality.

Sensitivity maps can be generated which show spatial sensitivity of a particular excitation-detection coil combination to pixel perturbations within the object space, i.e. perturbations within each pixel of the imaging area. Sensitivity maps are widely used to solve the inverse problems in image reconstruction, as they describe the unique conductivity distribution to pixel perturbations for the given sensor array. These maps can be calculated by either direct measurements, analytical approximation, or by numerical approaches. In this case, sensitivity maps were produced from dot production of B field values theoretically calculated using Biot-Savart law approach from a simplified model, and compared with FEM simulations using Maxwell Ansoft software.

Figure 3:
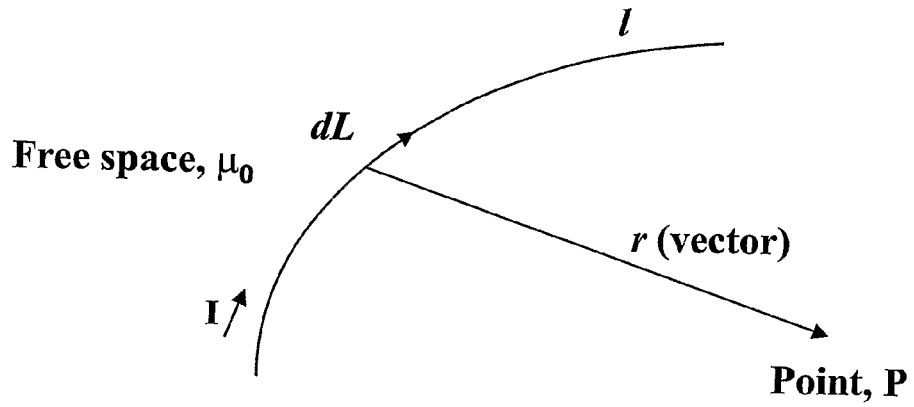
FIG. 3 is diagram showing the calculation of the magnetic field produced by the coils of the FIG. 1.

As shown in FIG. 3, Biot-Savart Law reveals that a magnetic field B will be produced by a short segment of wire dL, carrying current I, in accordance with the following formula:

$$B = \frac{\mu_0}{4\pi} \oint_l \frac{I \cdot dL \times r}{r^3} \tag{1}$$

where the direction of dL is in the direction of the current and the vector r points from the short segment of current to the observation point P where the magnetic field is computed. For a current flowing in a coil, integration is always required to find the total magnetic field at the point produced by an entire loop of coil. The constant $\mu_0$ is the permeability of free space, i.e., $4\pi \times 10^{-7}$ H/m.

For a coil pair, sensitivity between coils can be calculated by as being proportional to the formula $B_i \cdot B_j$, where $B_i$ and $B_j$ are the magnetic field densities produced when excitation coil (i) and sensing coil (j) are excited with unit current respectively.

A program can be implemented for B field and then sensitivity map computation for a square coil pair using the following steps

- Define the coils of a sensor array, mainly the (x, y, z) coordinates of the coils' turning points.
- Split a coil into a number of small current elements and then determine the start and stop (x, y, z) positions of each element.
- Compute the x, y and z components of the B field at point P(x, y, z) using equation (1).
- The computation is continued until the B fields at all points on the sensing plane are calculated for both excitation coil and detection coil.
- Determine the sensitivity map for this particular coil pair by taking the dot product of the fields produced by the excitation coil and the detection coil.

The computation time for map generation is mainly determined by the number of pixels divided across the sensing plane. Considering the compromise between computation time and resolution, the height (y-axis) and width (z-axis) of the gate are equally divided into a 51 by 20 grid respectively, yielding 1020 pixels for each sensitivity map. This partition makes a map resolution of approximately 4 cm×4 cm in this embodiment.

Figure 4A:
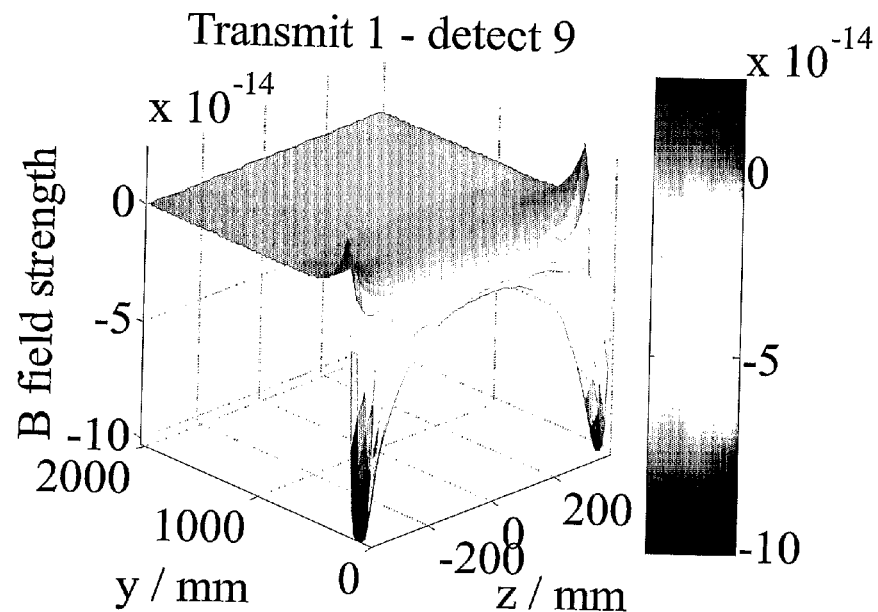
FIGS. 4a and 4b are sensitivity maps for certain coil pairs of the system of FIG. 2
Figure 4B:
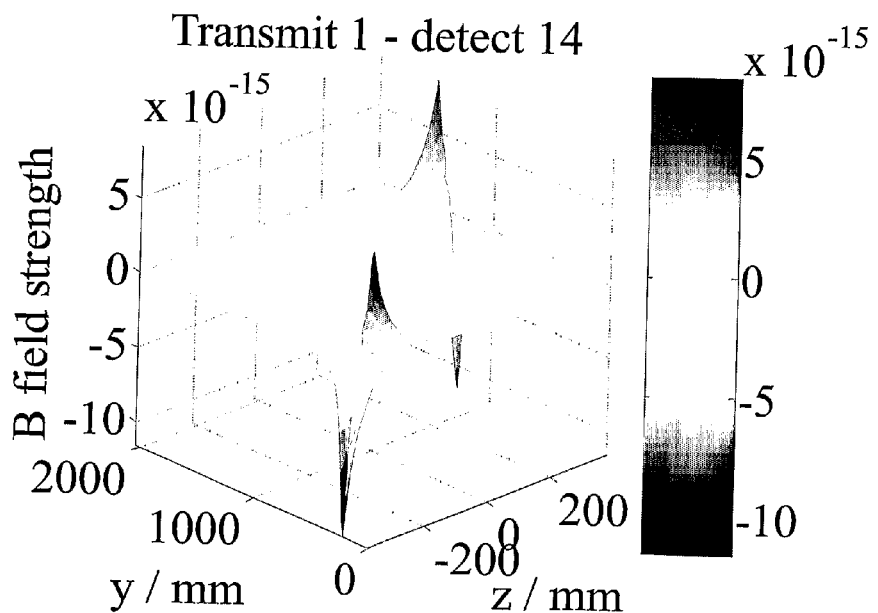

FIG. 4a shows one primary map of the system produced by the approach as given in the preceding section when the bottom transmitter coil, coil 1, is excited and the receiver coil directly opposite it, coil 9, acts as detector. FIG. 4b shows the map when coil 1 is excited and the receiver coil six from the bottom, coil 16, acts as detector. Other maps are not given here but their general format can be seen from these. The maps are produced using a surf function on 20×51 pixels for adequate representation.

The map distributions show the general trends. The overall sensitivity reduces as the excitation and detection coils are separated further in terms of signal changes shown in the B-field strength. For each coil pair, as shown by its absolute value, the sensitivity increases in the region approaching the coils due to the intensified magnetic field coupling in these positions.

The response of the coil array is very three dimensional, depending on the sensing plane.

Assuming the object materials are linear and isotropic in electrical and magnetic properties, the physical principle for electromagnetic induction problems can be described as a diffusion equation, written in terms of magnetic vector potential A for the sinusoidal waveform excitation cases, $$\nabla^2 A + j\omega\mu A = -\mu J_{coil} \tag{2}$$

Here, $J_{coil}$ denotes the source current density (A/m$^2$) passing through the excitation coil. Having obtained the vector potential A, the B field can be computed using $B=\nabla \times A$. A numerical analysis method was used in one embodiment, which can be achieved using electromagnetic finite element method (FEM).

The sensor geometry was simulated using a commercial 3D finite element package, which offers a piecewise solution to field problems by splitting the problem into a series of small tetrahedral elements over which the field values are approximated. A problem region was solved which was 9 times the volume of the sensor model to ensure the applied boundary conditions did not over constrain the solution. The surrounding air was assigned by the material property of a vacuum.

In the sensor model, the coils are simplified as a single conductor with a square cross-section of 10 mm×10 mm. A total of 59053 tetrahedral elements were meshed to ensure that the simulations converged to 0.25% target error after 13 computation passes. The time for one-coil excitation simulation is around 2 hours, thereby requiring 32 hours in total for 16 coil excitations (8 transmitters and 8 receivers).

The primary sensitivity maps calculated with B fields extracted from simulations are similar to those of FIGS. 4a and 4b. A conductor with 1 cm square cross-section in FEM is equivalent to a coil of 100 turns in the Biot-Savart approach. Both maps for the same coil pair shown in FIG. 4 and FIG. 6 appear to agree well with a magnitude error within 8%. The inverse problem for EMT is to convert the measured data into an image, which represents the conductivity distribution. This is typically an ill-posed and ill-conditioned problem as the number of independent measurements is usually far less than the number of pixels for an image. The reconstruction is further complicated by the soft field effect, whereby the object material changes both the magnitude and direction of the interrogating field.

However, for small changes in the pixel values, we can make a linear approximation with D=SD, where D is the measurement vector (length M where M is the number of transmitter/receiver pairs), P is the image pixel vector (length N where N is the number of pixels), and the matrix S is known as the sensitivity matrix (also called as Jacobian matrix) on an M×N basis. Jacobian matrix S can be formed by the sensitivity coefficients of the relevant coil pairs. For example, in this embodiment, S matrix is a 64×1020 matrix, where 64 represents 8×8 measurements and 1020 the image pixels. The matrix A is usually not inverted as it is not generally square and in any case is ill-conditioned.

Rather than computing the least-squares solution P which would be unstable due to the ill-conditioning of S some regularisation is required. In one embodiment the Tikhonov regularized solution $$P=(S^T S+\alpha I)^{-1} S^T D$$

Is used, which is the minimum of $\|D-A\cdot P\|^2+\alpha^2 \|D\|^2$, where $$\|x\| = \sqrt{\sum_k x_k^2}$$

and the superscript T indicates transpose. I is the identity matrix. Here $\alpha>0$ is a regularisation parameter that controls the trade-off between fitting the data and smoothness of solution.

Other embodiments involve other regularization methods including iterative solution methods (Landweber or conjugate gradient least squares for example), Total Variation Regularization, truncated singular value decomposition. In addition the range of the pixel values can be constrained. Other reconstruction techniques can equally be used.

Therefore it is possible, by using a number of different techniques, to generate a 2-dimensional image of the imaged area from the signals from the sensor coils 16.

In the case where an image is not required but improved accuracy is required for detection of objects of a certain size in particular zones, the above method is modified so that the pixels are replaced by zones, and the solution of simultaneous equations for the volume of conductive material in each zone computed using data measured from a plurality of driven and sensing coils.

Figure 5:
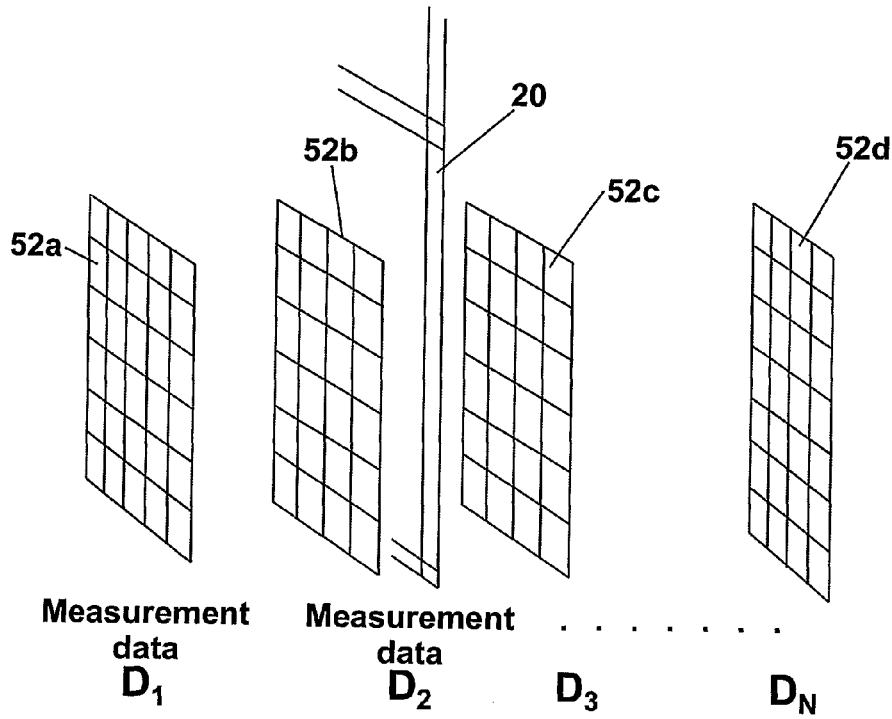
FIG. 5 is a diagram showing operation of the system of FIG. 1 in one mode of operation.
Figure 6:
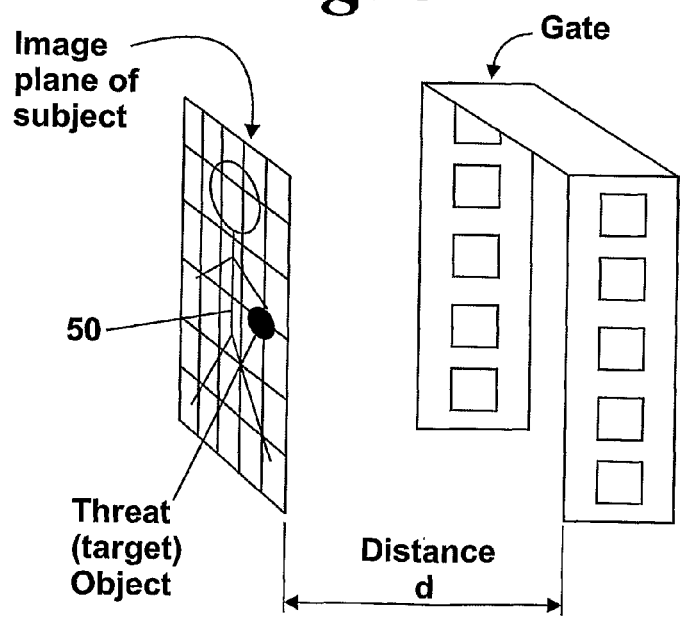
FIG. 6 is a further diagram of the system of FIG. 1 in the same mode of operation.

Referring to FIGS. 5 and 6, in one mode of operation the control system is arranged to generate a planar image of a person 50 as they walk through the gate 20. To do this it performs a number of scans as the person 50 moves through the gate 20, and for each scan the position of the person is determined using the video cameras 44, 46 and the control system defines a nominal image plane 52a, 52b, 52c, 52d in which the person is located, and which forms the image plane for that scan. Therefore, for each scan a separate set if image data D1, D2, D3 can be acquired, each set including a value for each pixel of the two dimensional image.

When the total number N of data sets has been acquired, they can be combined by the control system to form a single combined data set. This is a plane image data set, with data for each pixel being a combination of the corresponding values from each of the image sets. i.e.

$$D^T_{NEW}=[D^T_1, D^T_2 D^T_3 \ldots D^T_N]$$

The system is then arranged to find the pixel values P using:

$$D_{NEW}=S_{NEW}P$$

Where $S_{NEW}$ is a three-dimensional sensitivity matrix giving sensitivities for each pixel of the image for each position of the imaging plane, for each transmitter/receiver coil pair. This relationship can be inverted to find the image P making use of the measurements from the coil combinations and the signal profile as the person passes through the detector using the methods described earlier.

Figure 7:
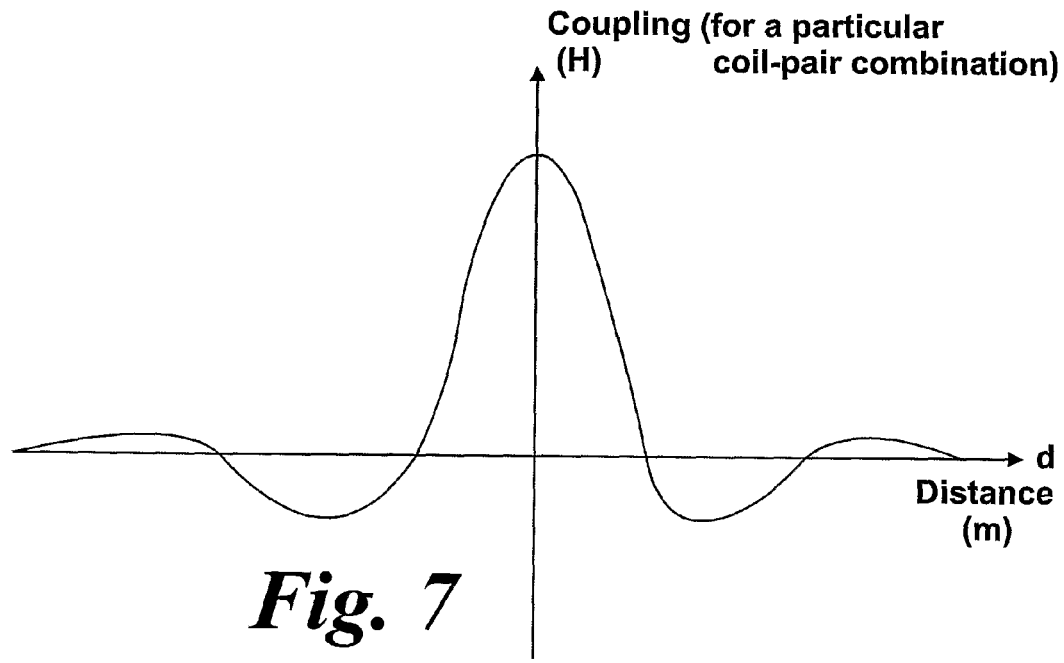
FIG. 7 is a graph showing generally how coupling of coil pairs of the system of FIG. 1 varies with distance from the coils of that system.
Figure 8:
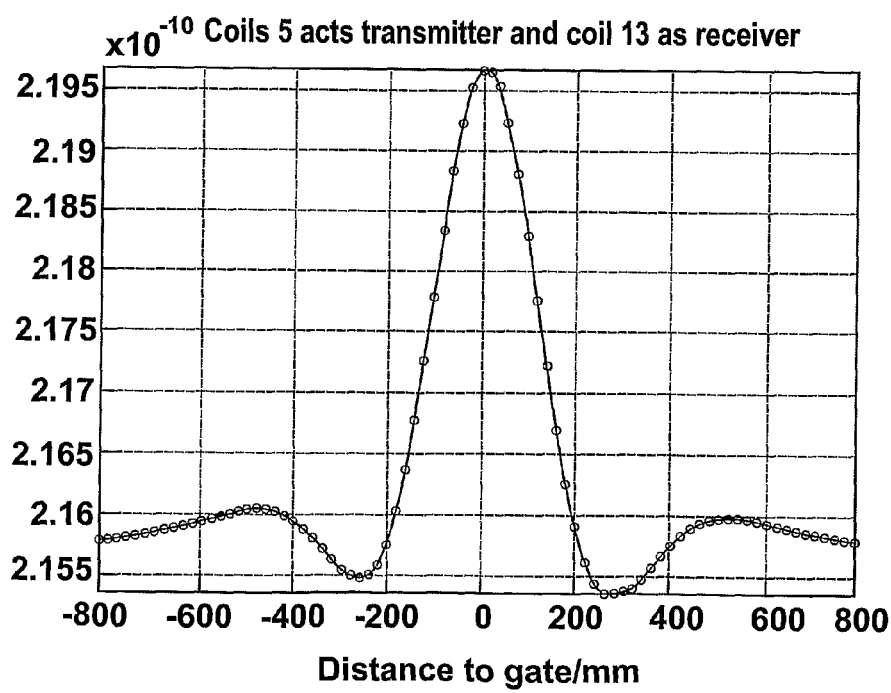
FIG. 8 is a specific example of a graph similar to that of FIG. 7 for a specific coil pair of the system of FIG. 1.

Referring to FIG. 7, the sensitivity for each transmitter/receiver coil pair varies with the distance d in a manner which can be calculated or measured. FIG. 8 shows an example for one of the pairs of coils in the system of FIGS. 1 and 2.

Referring to FIGS. 9a, 9b and 9c, in another mode of operation the control system is arranged to control the signals to the transmitter coils 12 and to monitor the signals from the receiver coils 16 repeatedly so as to generate a series of plane images of the imaging area 22 as a person 50 walks through the frame 20 and therefore through the imaging area. For each plane image, each of the transmitter coils 12 is activated in turn in a respective transmission period, and during each transmission period, the signals from each of the detector coils 16 is measured and recorded. These measurements for all combinations of transmitter coil and detector coil are combined to form a measurement matrix. This, together with the sensitivity matrix, is then used to determine pixel vectors for the image pixels making up the plane image.

In a modification to this time division multiplexing embodiment, in order to reduce scanning times, and therefore be able to increase the amount of scanning data that can be collected for a single person passing through the scanner, frequency division multiplexing is used. This can be either as well as or instead of the time division multiplexing. In this case, two or more of the transmitter coils 12 are arranged to transmit simultaneously, each at its own frequency. These simultaneous transmissions will produce a signal in each of the receiver coils 12 which includes components from each of the active transmitter coils. These components can be separated or distinguished on the basis of their different frequencies, using appropriate filtering, so that measurements for a plurality of transmitter/receiver pairs can be made simultaneously. More generally other modulation schemes could be employed to distinguish the coupling between particular coil combinations.

In the mode of operation described above the system is arranged to build up a two-dimensional image of the person 50. However, as the person walks through the frame 12 their arms 52 and legs 54 move in the longitudinal x direction relative to their body 56, and therefore the central vertical plane through the person's body 56 will contain different parts of the person's body as they walk. Therefore, referring to FIGS. 9a, 9b and 9c, in another mode of operation the processor 42 is arranged to analyze the frame of the video image of the person recorded at each time that an EM image from the coils 12, 16 is generated, to identify which parts of the person 50 are within a single imaging plane and therefore within that EM image, and how far those parts have been displaced in the x direction relative to the central plane through the person. Image data relating to each part of the person from each of the plane images can then be combined to build up an image data set relating to the person in a neutral stance with both arms and both legs aligned in a single plane. For example the EM image taken as the leading arm and leg of the person enter the imaging area, as shown in FIG. 9a will contain data relating to that arm and leg, and the EM image taken as the trailing arm and leg of the person leave the imaging area, as shown in FIG. 9c will contain data relating to that arm an leg. This data can be combined with the data from the EM image generated when the person is centrally located within the imaging area 22 as shown in FIG. 9b to build up a data set including data relating to all parts of the person, including any articles they are carrying with them. This data set can be used to generate an image for human viewing, and can also be analyzed by suitable image processing algorithms to determine whether it contains features representing a threat, for example if the data suggests the presence of a gun or a knife being carried by the person.

It will be appreciated that, in this mode, as the final image data set is of a planar image, the video images are used to determine the displacement of each imaged feature in each EM image from a reference position within that plane, and the processor 42 is arranged to shift each feature back to its reference position. As well as displacements in the x direction, displacements in the y and z directions can also be detected and corrected for in generating the final data set.

Referring to FIGS. 10a, 10b and 10c, in another mode of operation the processor 42 is arranged to analyze the video images to determine the position of the person 50 relative to the imaging area 22 and the coils 12, 16, and therefore to identify different planes through the person that have been imaged by the EM images, and their relative positions within the person 50. The processor 42 is then arranged to combine the plane EM image data sets to form a 3 dimensional tomographic image data set of the person, including any articles they are carrying with them. Again this can be used to display an image and analyzed by appropriate image processing algorithms to identify any possible threats.

Figure 11:
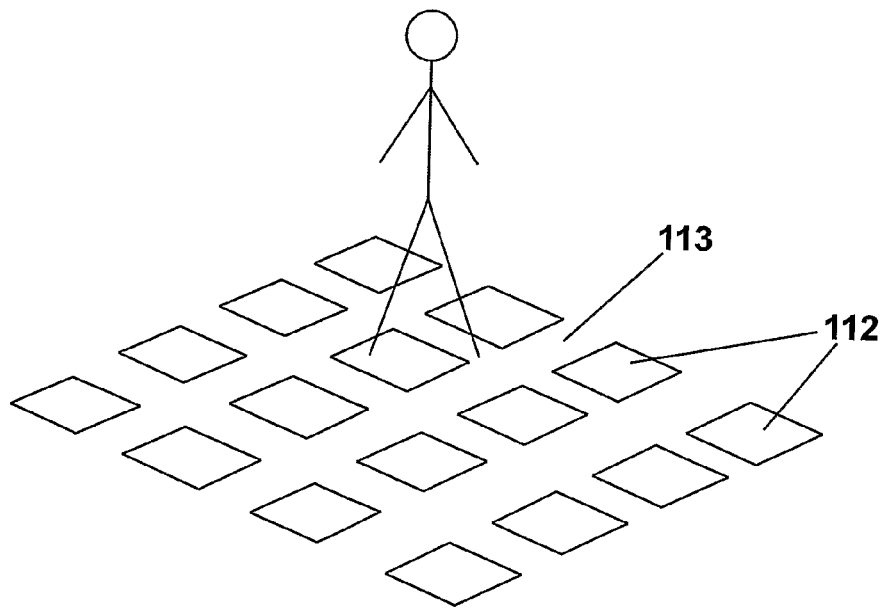
FIG. 11 is a schematic view of a detection system according to a second embodiment of the invention.

Referring to FIG. 11, in a second embodiment of the invention the scanning system comprises a single array of coils 112 which are located substantially within a single plane in a floor structure 113 over which a person to be scanned can walk. In this case each of the coils can have a current passed through it by the control system so that it acts as a transmitting coil, and can also have the current through it measured by the control system so that it can act as a receiver coil. As a person walks over the scanner, a sequence of image data sets, which in this case are three-dimensional, are acquired, each corresponding to a single three-dimensional image frame. Each image will therefore comprise a number of volume elements or voxels. For each image frame, each of the coils is activated as a transmitter coil in turn, and for each emitting coil, the signals produced in each of the other coils, which are then acting as receiving coils, are measured and recorded. This produces a set or matrix of measurements, one for each transmitter, receiver pair, which can be used together with a sensitivity matrix to generate image data sets, or other data sets for analysis, as in the first embodiment. The image data sets from the image frames can be combined as in the first embodiment. Video imaging can again be used to determine the position of the person, and of different parts of the person, in each frame, so that changes in those positions between frames can be corrected for when combining the frames.

In a modification to this embodiment the planar array of coils 112 are used only as transmitter coils, and a planar array of detectors coils, or other detectors, is arranged in the ceiling over the coils 112. These transmitter and receiver arrays are operated in a similar manner to the linear arrays of FIG. 2, but each image data set represents a three-dimensional image. If the system is used to generate data for analysis other than imaging, the data sets comprise data relating to a number of volume elements, or voxels, of the scanned or imaging space through which the person is walking. In further modifications, the arrays of transmitters and receivers can be located in walls on opposite sides of the scanned or imaged space, or in building furniture, or indeed in a variety of configurations.

The invention claimed is:

1. A detection system comprising a plurality of magnetic field generators and a plurality of magnetic field detectors located adjacent to a detection area, and a control system arranged to generate magnetic field using the generators, and, for each of the generators, to make measurements of the magnetic field generated using each of the detectors, a processor arranged to process the measurements to generate a plurality of sets of data characterizing the detection area as an object moves through the detection area and to combine the sets of data to form a resultant data set, wherein said resultant data set is representative of a planar image, and a displacement sensor arranged to detect a displacement of a part of the object away from a reference position, wherein the processor is arranged to correct for the displacement when combining the sets of data and wherein said correction shifts a detected feature back to the reference position.

2. A detection system according to claim 1 which is a security detection system in which the generators and detectors are mounted on support means arranged to allow a person to walk through the imaging area.

3. A detection system according to claim 1 further comprising a movement sensor arranged to measure changes of position of at least a part of an object relative to the generators and detectors and to use the changes of position when combining the sets of data.

4. A detection system according to claim 3 wherein the data sets are combined to form a combined data set that includes data for each element in a plane of elements, wherein the data for each element includes data from each data set.

5. A detection system according to claim 1 wherein the processor is arranged to combine the sets of data to produce a tomographic data set representing the object.

6. A system according to claim 1 wherein the reference position is a position relative to at least a part of the object and the displacement is a displacement relative to at least a part of the object.

7. A system according to claim 1 wherein the detectors comprise detector coils, and the control system is arranged to make the measurements by detecting electrical signals induced in the detector coils.

8. A system according to claim 1 wherein the generators comprise generator coils and the control system is arranged to generate the magnetic field by generating an electric current in the generator coils.

9. A system according to claim 1 wherein at least one of the generators is arranged to operate also as a detector.

10. A system according to claim 1 wherein at least some of the generators or detectors are arranged in a planar array.

11. A system according to claim 1 wherein the generators and the detectors are located in a floor or wall structure or building furniture.

12. A method of analyzing an object comprising providing a plurality of magnetic field generators and a plurality of magnetic field detectors located around a detection area, generating magnetic field using each of the generators, for each of the generators, making measurements of the magnetic field produced using each of the detectors, processing the measurements to generate a plurality of sets of data characterizing the detection area as an object moves through the detection area and to combine the sets of data to form a resultant data set, wherein said resultant data set is representative of a planar image, detecting a displacement of a part of the object away from a reference position, and correcting for the displacement when combining the sets of data, wherein said correction shifts a detected feature back to the reference position.

13. A method according to claim 12 in which the generators and detectors are mounted on support means arranged to allow a person to walk through the detection area.

14. A method according to claim 12 further comprising measuring changes of position of at least a part of an object relative to the generators and detectors and using the changes of position when combining the sets of data.

15. A method according to claim 12 further comprising combining the sets of data to produce a tomographic data set representing the object.

16. A method according to claim 12 wherein the reference position is a position relative to at least a part of the object and the displacement is a displacement relative to at least a part of the object.

17. A method according to claim 12 wherein the generators comprise generator coils and the magnetic fields are generated by generating electric current in the generator coils.

18. A method according to any of claim 12 wherein the detectors comprise detector coils and the magnetic fields are measured by measuring induced signals in the detector coils.

* * * * *